United States Patent [19]

Fleck et al.

[11] 4,182,861
[45] Jan. 8, 1980

[54] FLUORESCENT 1,2,3-TRIAZOLE DERIVATIVES OF 3-PHENYLCOUMARIN

[75] Inventors: Fritz Fleck, Bottmingen; Hans Balzer, Munchenstein; Horst Aebli, Basel, all of Switzerland

[73] Assignee: Sandoz Ltd., Basel, Switzerland

[21] Appl. No.: 755,459

[22] Filed: Dec. 30, 1976

Related U.S. Application Data

[63] Continuation-in-part of Ser. No. 572,005, Apr. 28, 1975, Pat. No. 4,006,158, which is a continuation of Ser. No. 695,330, Jan. 3, 1968, abandoned.

[30] Foreign Application Priority Data

Jan. 5, 1967 [CH] Switzerland .................... 108/67

[51] Int. Cl.$^2$ .................. C07D 405/04; C07D 405/10; C09K 1/02
[52] U.S. Cl. .................................... 542/441; 548/256; 542/431
[58] Field of Search ................ 260/240 D, 308 A; 542/431, 458, 441

[56] References Cited

U.S. PATENT DOCUMENTS 3,869,469  3/1975  Neuner et al. ............... 260/308 A

FOREIGN PATENT DOCUMENTS 478835  11/1969  Switzerland .................. 260/308 A

*Primary Examiner*—Alton D. Rollins
*Attorney, Agent, or Firm*—Gerald D. Sharkin; Richard E. Vila; Thomas C. Doyle

[57] ABSTRACT

Polyester, cotton, polyamide and polyacrylonitrile fabrics and foils of polyvinylchloride are optically brightened by the addition of a compound of the formula

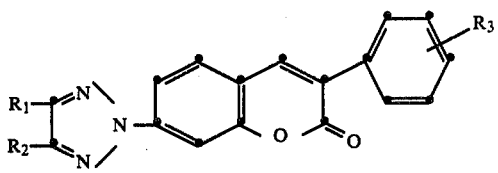

in which each of
$R_1$ and $R_2$ represents a hydrogen atom or an aliphatic, alicyclic, araliphatic, halogen- or alkyl-substituted araliphatic, aromatic, or halogen- or alkyl-substituted aromatic radical,
$R_3$ represents a hydrogen or halogen atom or a low molecular weight alkyl or alkoxy radical.

4 Claims, No Drawings

FLUORESCENT 1,2,3-TRIAZOLE DERIVATIVES OF 3-PHENYLCOUMARIN

This application is a continuation-in-part of application Ser. No. 572,005 filed Apr. 28, 1975, now U.S. Pat. No. 4,006,158 which, in turn, is a continuation of application Ser. No. 695,330, filed Jan. 3, 1968 and now abandoned.

The present invention provides compounds of the formula I

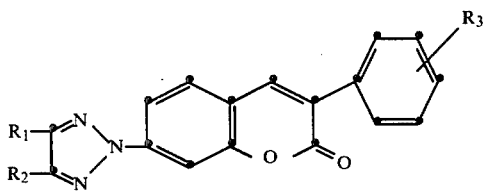

in which each of $R_1$ and $R_2$ represents a hydrogen atom or an aliphatic, alicyclic, araliphatic, halogen or alkyl substituted araliphatic, aromatic, or halogen or alkyl substituted aromatic radical, $R_3$ represents a hydrogen atom or a low molecular weight alkyl or alkoxy radical; the phrase "low molecular weight" as applied to alkyl and alkoxy designates such radicals with 1 to 6 carbon atoms.

The compounds of formula I fluoresce when in solution.

The present invention also provides a process for the production of the compounds of formula I, characterized in that a hydrazone oxime of the formula II

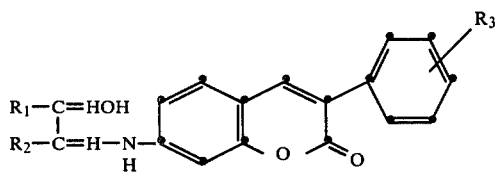

wherein $R_1$, $R_2$ and $R_3$ have the above significance, is cyclized to give a 1,2,3-triazole compound by heating in the presence of a solvent and an anhydride of a low molecular weight fatty acid; said anhydrides are those containing up to 6 carbon atoms. Preferably this heating is effected in the presence of a tertiary base.

Specific examples of suitable radicals $R_1$ and $R_2$ are: hydrogen, methyl, ethyl, isopropyl, phenyl, diphenyl, benzyl, tolyl, methoxyphenyl, butyl, chlorophenyl, chlorotolyl, styryl, chlorostyryl, cyclohexyl, cyclopentyl, naphthyl, xylyl, dichlorophenyl, nonyl, cetyl, stearyl, dimethylbenzyl.

Suitable values for the radical $R_3$ are hydrogen, methyl, ethyl, butyl, isopropyl, methoxy, ethoxy, chlorine or bromine.

The starting material hydrazone oximes of the formula II may be produced in known manner, for example by reacting β-nitrosoketones with 3-phenyl-7-hydrazino-coumarin which may be substituted if necessary.

As indicated above, when $R_1$ or $R_2$ represents an aromatic or araliphatic radical, the aromatic or araliphatic radical may be substituted with alkyl (for example methyl) or halogen (especially chlorine), or both alkyl and halogen.

The processes hitherto described in the literature on the subject for cyclizing hydrazine oximes give rise to bad yields in cyclization product. It is therefore surprising that the compounds of formula I can be obtained with good yields merely by heating, as described in detail hereinafter, a hydrazone oxime of the formula II with, for example, acetic anhydride in the presence of a solvent and optionally of a tertiary base. The compounds of formula I can be freed of by-products and purified in manner known per se.

Suitable anhydrides of low molecular weight fatty acids for use in the process of the invention are those of acetic acid and propionic acid; suitable solvents are, for example, dimethylformamide, dimethylacetamide, dimethylsulphoxide, N-methylpyrrolidone and cyclohexanone. The solvent is used, depending on the solubility of the hydrazone oxime, in the amount which generally comes to three to five times in quantity of hydrazone oxime. Suitable tertiary bases the presence of which favourably influences the reaction are, for example pyridine or technical mixtures of pyridine bases. The fatty acid anhydride and the tertiary base are used in excess, it being permissible for the weight ratios to vary within wide limits.

Temperatures favourable for effecting the reaction of the process of the invention are between 25° and 200° C., preferably between 50° and 150° C.

The compounds of formula I are colourless or almost colourless substances which, when dissolved in a solvent therefor, strongly fluoresce violet-blue to blue; the compounds of formula I are exceedingly suitable as optical brighteners or marking agents for organic materials or as scintillating agents.

Organic materials, which may be optically brightened by the compounds of formula I, are primarily those of synthetic, fibre forming polyesters, polyamides, polyurethanes, polyolefins, polyvinylchloride, polyvinylidenechloride, polyacrylonitrile, modified polyacrylonitrile, cellulose triacetate or diacetate, further also oils, fats, waxes, lacquers, resins and cosmetic preparations.

The compounds of formula I can be used dissolved in solvents or in finely divided form, for example as aqueous dispersions, when they are to be used in the treatment of textile materials. They can be successfully incorporated into spinning or pressing masses or may be added to monomers or a pre-condensate used for the production of plastics. Their use with polyester or mixed polyester fabrics is advantageously affected by padding in an aqueous dispersion of the new compounds, whereupon drying and thermal fixing are effected. The concentration of the new compounds, depending on the manner of their use, may amount to 0.01 to 0.5%, based on the weight of the material to be brightened. The brighteners produced according to the invention may be used alone or in combination with other brighteners, as well as in the presence of surface active agents, for instance washing agents or in the presence of bleaching agents.

In comparison to the known 1,2,3-triazole derivatives of 3-phenyl-7-aminocoumarin described in French Patent Specification No. 1,358,820, the triazoles of the invention are characterized by more neutral shades of white and a better solubility in organic media. They are excellently fast to light and stable to heat and also stable towards neutral or acid bleaching agent solutions.

In the following Examples the temperatures are stated in degrees Centigrade; the parts are parts by weight.

EXAMPLE 1

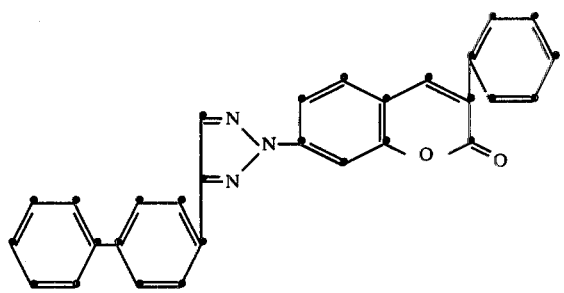

20 parts of hydrazone oxime of formula II ($R_1$=H, $R_2$=p-diphenyl, $R_3$=H) are mixed with 40 parts of dimethylformamide, 60 parts of acetic acid anhydride and 60 parts of pyridine and stirred at 100° for two hours. After the cyclization is complete, about half of the solvent mixture material is distilled off and, on cooling of the reaction mixture, light brown crystals are obtained which are capable of purification by recrystallization from chlorobenzene and treatment with charcoal. The resulting compound of the above formula, when dissolved in chlorobenzene, shows a very strong, blue fluorescence.

When in the above hydrazone oxime $R_2$ is styryl or p-chlorostyryl, the hydrogen atom $R_3$ is replaced with chlorine, methyl, methoxy, n-butoxy, isopropyl or t-butyl, the resulting compounds likewise fluoresce with a strong blue colour when dissolved; they are extremely suitable for optically brightening plastics.

EXAMPLE 2

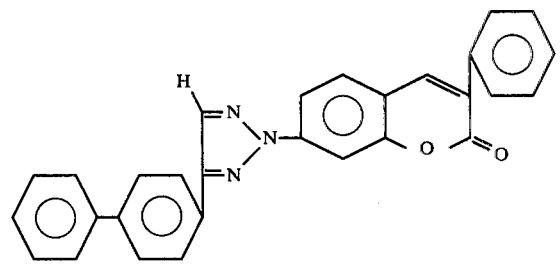

20 parts of crude hydrazone oxime of formula (II), in which $R_1$=H, $R_2$=p-biphenylyl and $R_3$=H, melting between 263°–270° are mixed with 40 parts of dimethylformamide, 60 parts of acetic acid anhydride and 60 parts of pyridine. There is obtained a reddish brown solution which is agitated for two hours at 25°–30° and then for further two hours at 55°–60°. After this time the reaction mixture which contains no more of the hydrazone oxime is boiled until half of its volume of the volatile ingredients is evaporated. The remaining part is cooled and filtered by suction. The residue is washed with methanol, dried and the light brown product obtained is purified by recrystallization from chlorobenzene and treatment with charcoal.

There are obtained 16.5 parts (86% of the theoretical yield) of light yellow crystals of the compound of the formula indicated above, melting at 266°–267°, which shows a very strong violet fluorescence when dissolved in chlorobenzene. It absorbs ultraviolet radiations when dissolved in dimethylsulfoxide, the maximum of absorption resulting at a wave length λ of 366 nm.

If in the hydrazone oxime of formula (II) $R_1$ has the signification mentioned in the following table and if one proceeds as described in this example one obtains the compounds $C_1$, $C_2$, $C_3$, $C_4$ and $C_5$ of formula (I), in which $R_3$ is a hydrogen atom, $R_2$ p-biphenylyl and $R_1$ has the signification mentioned in the following table, which table also indicates the melting points F in °C., the yields in % of the theoretical one and the λ max. in dimethylsulfoxide of these compounds.

| comp. | $R_1$ | F | yield | λmax. |
|---|---|---|---|---|
| $C_1$ | $CH_3$ | 200–201 | 64 % | 367 nm |
| $C_2$ | $C_2H_5$ | 217–218 | 65 % | 368 nm |
| $C_3$ | n-$C_4H_9$ | 188–189 | 61 % | 368 nm |
| $C_4$ | ⌬ (phenyl) | 242–244 | 45 % | 372 nm |
| $C_5$ | ⌬–⌬ (biphenylyl) | 287–288 | 42 % | 371 nm |

All the compounds are excellently suitable for the optical brightening of spinnable synthetic resins, especially of polyester, by incorporating them into said resins.

The hydrozone oximes used in this examples as starting material can be prepared by condensing equivalent quantities of the corresponding α-oximino ketones with 7-hydrazino-3-phenylcoumarin. The 7-hydrazino-3-phenylcoumarin can be obtained according to H. Hausermann, U.S. Pat. No. 3,123,617 assigned to I. R. Geigy A.G., Basle, Switzerland, in the presence of dimethylformamide and 50% aqueous acetic acid, the yield being more than 90% of the theoretical one.

The hydrazone oximes are obtained as orange yellow crystalline powders which can be used as starting material for cyclization without being purified. In the following table the crude hydrazone oximes used as starting material for the preparation of the compounds of formula (I) specified in the table mentioned before, are specified by their melting points in °C. These hydrazone oximes are compounds of formula (II), wherein $R_3$ represents a hydrogen atom, $R_2$ biphenylyl and $R_1$ the radicals mentioned in the following table.

| $R_1$ | melting points |
|---|---|
| $CH_3$ | 243–250° |
| $C_2H_5$ | 208–215° |
| n-$C_4H_9$ | 221–228° |
| ⌬ (phenyl) | 232–241° |
| ⌬–⌬ (biphenylyl) | 225–237° |

EXAMPLE 3

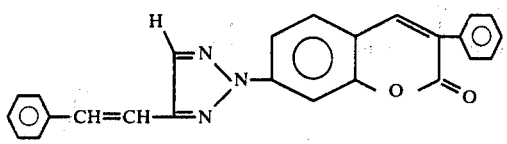

20.5 parts of the hydrazone oxime of formula (II), in which $R_1=H$, $R_2=$sytryl and $R_3=H$, are mixed with 40 parts of dimethylformamide, 60 parts of acetic acid anhydride and 60 parts of pyridine, and agitated at 25°-30° for two hours. The reddish brown solution obtained is heated and maintained at 80° until there is no more unreacted starting material in it (1-2 hours). Then the reaction mixture is treated as described in example 2 and the resulting product is purified by crystallization from chlorobenzene and treatment with bleaching earth and small quantities of zinc dust. There are obtained 10.2 parts (52% of the theoretical yield) of the compound of the formula indicated above, as light yellow crystals melting at 233°-234°.

This compound shows a very strong blue-violet fluorescence when dissolved in chlorobenzene and is very suitable for the optical brightening of synthetic resins.

If there is used as starting material a hydrazone oxime of formula (II) wherein $R_2$ represents p-chlorostyryl instead of sytryl and if one operates as described above the resulting p-chlorostyryltriazol derivative is obtained in a yield of 41% of the theoretical one. It melts at 268°-270° and possesses very similar properties to the compound mentioned above which is not substituted by a chloro atom.

The hydrazone oximes of formula (II) used as starting material for the preparation of the above-mentioned styryl and p-chlorostyryl derivatives may be prepared according to the method described in example 2 by condensing-7-hydrazino-3-phenylcoumarin with the corresponding α-oximo-benzal-acetone derivative, which derivative can easily be prepared by reacting isonitroso-acetone (see Houben-Weyl, *Methoden der organischen Chemie*, fourth edition 1965, vol. X/3, Stickstoffverbindungen I, Teil 3, page 187) with benzaldehyde or p-chlorobenzaldehyde respectively in aqueous potassium hydroxide solution (C. Harries and W. S. Mills, *Liebigs Annalen der Chemie* 330, 248 (1904).

The melting point of the hydrazone oxime of formula (II), in which $R_1=R_3=H$ and $R_2=$styryl, is 224° and the melting point of the hydrazone oxime of formula (II), in which $R_1=R_3=H$, and $R_2=$p-chlorostyryl, is 134°-136°.

EXAMPLE 4

10 parts of the compound prepared as in Example 1 or 2 are mixed with 2 parts of castor oil which has been sulphonated to a high degree and is available commercially under the name of Sandozol KB (Trade Mark registered by the firm Sandoz), 8 parts of the sodium salt of dioctylphenylpolyglycol ether hydroxy acetic acid containing 40 ethenoxy radicals per molecule, and 80 parts of water, and the mixture is worked in a comminuting apparatus, for example in a sand mill, until the majority of the mass has a particle size of 0.5-2. 100 parts of a fabric of poly-(ethyleneglycolterephthalate) are placed into a bath at 50°, which has the following composition: 300 parts of water, 5 parts of o-dichlorobenzene as carrier and 2 parts of the above described dispersion. The material is left for 15 minutes at that temperature and the bath is then heated to boiling temperature during 30 minutes, boiling is continued for 45 minutes and the fabric is treated at 70° in a bath containing 1.5 g/l octylphenyldecaglycol ether (bath ratio 1:40, duration 10 minutes). Warm rinsing and drying are then effected. The polyester fabric treated in this way is strongly brightened. The brightening is characterized by a very good stability to light and washing. When working is effected at 120°-130° in closed apparatus, a similar white effect is achieved without addition of a carrier.

Similar results are achieved when the foregoing is repeated using the compounds $C_1$ to $C_3$ of Example 2 or the compound of Example 3 in place of the compound of Example 1.

EXAMPLE 5

A mixed fabric of cotton/polyester, for example cotton/Diolen, is impregnated at room temperature by padding with a liquid containing 20 parts of the optical brightener dispersion described in Example 4 containing the compound of Example 3 in 1000 parts of water. The liquid taken up is reduced to 80% by squeezing, drying for 30 minutes at 60° is effected and thermal treatment for one minute at 200° is effected. The fabric becomes strongly brightened by this procedure, the degree of brightening being similar to that obtained in Example 4.

When there is used instead of the mixed fabric of this Example a polyester fabric (e.g. Dacron, Terylene or Diolen), the last mentioned fabric is brightened in manner similar to that for the mixed fabric.

When the compound of Example 3 is replaced by the compound $C_2$ or $C_3$ of Example 2, similar results are obtained.

EXAMPLE 6

A granulate of 6-polyamide (Grilon) is powdered in a mixing apparatus with 0.01-0.05% of its own weight of the compound $C_1$ described in Example 2 and melted in an apparatus usual for melt spinning for 30 minutes at about 300° under an atmosphere of nitrogen, stirred at that temperature for 15 minutes and then brought to the spinning temperature of 285°. At a pressure of 4-6 atmospheres (nitrogen) this mass is spun into a monofilament. The resulting fibres fluoresce intensely blue in daylight. They appear whiter and brighter than fibres produced under comparable conditions but without brightener. When using, instead of the compound $C_1$ compound $C_2$, $C_3$, $C_4$ or $C_5$, similar white effects are produced. When using polyester or polypropylene, instead of polyamide, and spinning is effected at 290° and 260° respectively, there are likewise obtained fibres of a higher degree of whiteness than comparative fibres produced without brightener.

EXAMPLE 7

100 parts of polyvinyl chloride are dissolved in a usual solvent, for example methylene chloride, 0.04% of its weight of either brightener produced according to Example 3 and dissolved in the same solvent are added and spinning according to the wet spinning process is effected to produce threads. The product is markedly brightened and has an excellent stability to light in comparison to threads spun without brightener.

EXAMPLE 8

100 parts of polyvinyl chloride mass (consisting of 65 parts polyvinyl chloride, 35 parts of a softener and 2%, based on the polymer, of a stabilizer) are mixed with 0.05–0.1 part of one of the brighteners obtained according to Example 1 or 2 (the brightener is dissolved in the softener), working up on a rolling mill is effected at 150°–160° for 10 minutes and the resulting material is drawn to form foils. In order to produce opaque foils 2.5% of titanium dioxide had been added to the mass before working up. The resulting foils have an improved appearance as compared with similar ones produced without brightener.

EXAMPLE 9

100 parts of dimethyl-terephthalate, 48.5 parts of ethylene glycol and 0.3 parts of a sodium-catalyst are mixed and heated for 3 hours at 200° in a nitrogen atomosphere. After this time there are added to the resulting precondensate 3 parts of the brightener $C_2$ and homogeneously distributed therein. The homogeneous mass is then heated for 30 minutes to 280° and then 10 hours under reduced pressure at this temperature. During this time there is introduced slowly nitrogren through a capillary tube. The reaction produce melts at 260°. It is obtained in the form of ribbons that, after cooling by spraying with cold water are cut into chips. Fibrous material spun in the usual manner from such chips is strongly brightened.

EXAMPLE 10

1000 parts of dimethyl-terephthalate, 665 parts of ethylene glycol, 0.55 part of manganese acetate, 0.18 parts of antimony trioxide and 0.6 parts of one of the brighteners mentioned in example 2 are mixed together and heated at 160° for two hours. The reaction is finished where distilling off at methanol ceases.

The resulting condensation product is then further heated to about 225° and mixed with 5 parts of titanium oxide and 0.3 part of phosphoric acid. The pressure is then reduced to 1 mm mercury gauge and the temperature elevated to 290°. It is maintained until the desired degree of polymerisation is obtained. The resulting mass is then spun to fibres according to known methods. These fibres are of a brilliant white which is exceedingly solid to washing and resistant to light.

EXAMPLE 11

In a vessel of stainless steel provided with a heating jacket there are mixed together in an atmosphere of pure nitrogen 388 parts of dimethyl terephthalate, 300 parts of ethylene glycol and 0.4 part of antimony oxide with heating at 200° (exterior temperature) and maintaining this temperature for three hours. During this time methanol distills off. To the reaction product there is then added at 190° a solution of 0.4 part of one of the brighteners cited in the examples 1 to 3 in 40 parts of ethylene glycol. No air should be present in the vessel containing the reaction mass during this operation. Once the brightener being incorporated thereto the temperature of the heating jacket is elevated to 285 in order to eliminate the ethylene glycol which at this temperature distills off.

To complete the reaction and the elimination of the ethylene glycol the pressure is reduced to 0.2 Torr. and the temperature maintained for three hours. During this time the reaction product is well agitated. The monofilament which can be spun from the polyester thus obtained has a high degree of whiteness.

We claim:

1. A compound of the formula

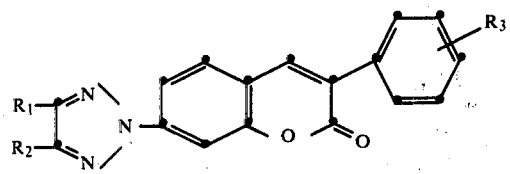

wherein
$R_1$ is hydrogen, methyl, ethyl, isopropyl, phenyl, diphenyl, benzyl, tolyl, methoxyphenyl, butyl, chlorophenyl, chlorotolyl, styryl, chlorostyryl, cyclohexyl, cyclopentyl, naphthyl, xylyl, dichlorophenyl, nonyl, cetyl, stearyl or dimethylbenzyl,
$R_2$ is diphenyl, styryl or p-chlorostyryl,
and
$R_3$ is hydrogen, methyl, ethyl, isopropyl, butyl, methoxy, ethoxy, chlorine or bromine.

2. A compound of the formula

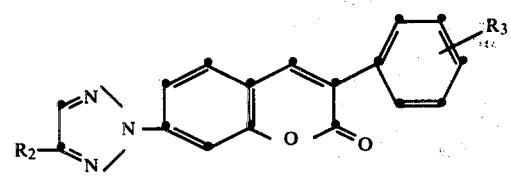

wherein
$R_2$ is diphenyl, styryl or p-chlorostyryl and
$R_3$ is hydrogen, chlorine, methyl, methoxy, n-butoxy, isopropyl or t-butyl.

3. A compound according to claim 2 having the formula

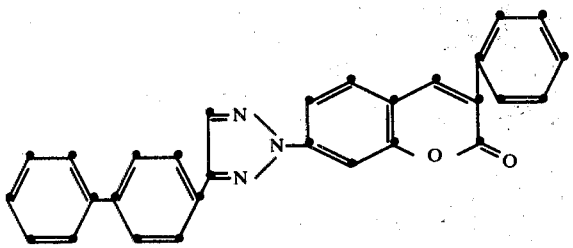

4. A compound according to claim 2 having the formula

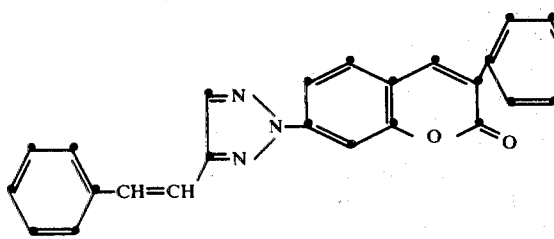

* * * * *